Figure 1:
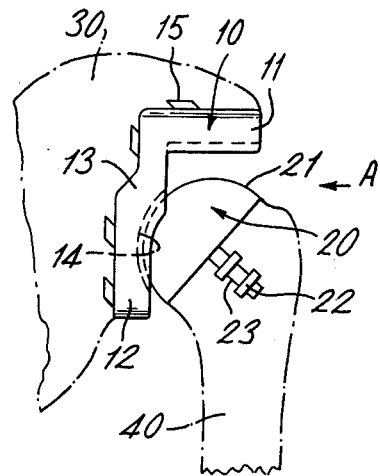

United States Patent [19]

Swanson et al.

[11] 4,042,980

[45] Aug. 23, 1977

[54] ENDOPROSTHETIC SHOULDER JOINT DEVICE

[75] Inventors: Sydney Alan Vasey Swanson, Carshalton; Brian Arnold Roper, London, both of England

[73] Assignee: National Research Development Corporation, London, England

[21] Appl. No.: 665,574

[22] Filed: Mar. 10, 1976

[30] Foreign Application Priority Data

Mar. 13, 1975 United Kingdom ............... 10540/75

[51] Int. Cl.² ............................................. A61F 1/24
[52] U.S. Cl. ..................................... 3/1.91; 128/92 C
[58] Field of Search ................................. 3/1.9–1.913, 3/1; 128/92 C

[56] References Cited

U.S. PATENT DOCUMENTS

| 3,839,742 | 10/1974 | Link ......................................... 3/1.91 |
| 3,852,831 | 12/1974 | Dee ............................................... 3/1 |
| 3,925,824 | 12/1975 | Freeman et al. ...................... 3/1.912 |

FOREIGN PATENT DOCUMENTS 2,400,650   7/1974   Germany ................................ 3/1.91

Primary Examiner—Ronald L. Frinks
Attorney, Agent, or Firm—Cushman, Darby & Cushman

[57] ABSTRACT

An endoprosthetic shoulder joint device has a scapular component of generally L-shape, usually with one arm longer than the other, and formed with a spherical concave bearing surface in its inner face to extend at least over the free end portion of the longer arm. If the concave surface extends in the shorter arm, the latter arm is thickened for this purpose. The concave surface can open into the edges of the L-shape, the longer arm is usually of cranked form, and the outer face is relieved for cement securement keying. The associated humeral component can be of conventional ball-headed, stemmed form, but is preferred as a spherical segmental form which is solid with a short stem projecting from its chordal face, or hollowed and grooved in its interior.

8 Claims, 3 Drawing Figures

ENDOPROSTHETIC SHOULDER JOINT DEVICE

This invention concerns prosthetic devices, and more particularly endoprosthetic shoulder devices.

Endoprosthetic devices for total arthroplasty of the shoulder joint have only been proposed in the last few years and it remains to be seen whether such devices as proposed so far prove clinically satisfactory in the longer term. This situation contrasts with that of corresponding devices for other joints, particularly the hip, and arises, among other things, from the large range of articulation of the natural shoulder joint and difficulty in effecting secure fixation of a prosthetic scapular glenoid component.

In order to meet this articulation requirement and fixation difficulty, the present invention provides an endoprosthetic shoulder joint device comprising: a humeral component including a bearing part defining a substantially part-spherical, convex bearing surface; and a scapular component including a generally L-shaped member having at least part of its inner face formed to define a substantially part-spherical, concave bearing surface; said bearing surfaces being engageable for mutual articulation between said components, and said part and said member being adapted remotely from said bearing surfaces for respective securement to the humerus and scapula.

Normally one arm of the L-shape will be longer than the other, and the concave bearing surface is then formed at least partly in this longer arm.

A principal feature of the proposed device is the L-shaping of the scapular component member. This derives from the consideration that, in severely rheumatoid shoulders, the rotator mechanism above the humeral head is usually so far destroyed as to be removable without further loss. Given such removal, the L-shaped member can be located with its longer arm and at least part of the concave bearing surface located across the site of the glenoid cavity and its other arm located on the underside of the acromion. Such shaping and location also allows secure fixation, this being preferred at present to involve the provision of a low relief configuration on the relevant remote surfaces of the member to key with bone cement. Furthermore, the concave bearing surface, which replaces the natural scapular glenoid cavity, can simulate the latter by being shallow and elongated and thereby enhance the ability for providing a suitably large range of articulation with the humeral component.

The humeral component should provide a convex bearing surface which affords the desired range of articulatory engagement with the concave bearing surface of the scapular component and, to this extent, the former component may be of known form comprising a ball at one end of a long intramedullary stem. However it is preferred that the humeral component define a spherically convex surface of approximately hemispherical extent and be in the general form of a hemispherical cap or solid have a relieved configuration remote from its convex surface which configuration is shallow relative to conventional intramedullary stems. As an indication of this degree of shallowness, the relieved configuration in the case of a solid component is presently preferred in the form of a stem having a maximum length approximately equal to the diameter of the associated convex surface. In any event, the preferred humeral component form requires a reduced bone removal and/or bone penetration compared to conventional forms.

Figure 2:
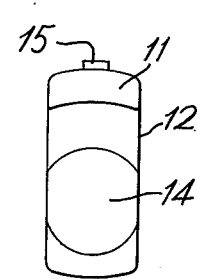
Figure 3:
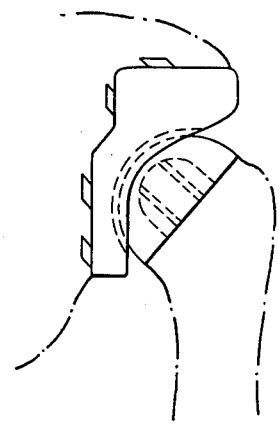

In order that the invention may be more fully understood, the same will now be described by way of example with reference to the accompanying drawings, in which:

FIG. 1 schematically illustrates in front view one embodiment of the invention in its intended location relative to a left shoulder, FIG. 2 illustrates the scapular component of FIG. 1 as viewed in the direction A of the latter figure, and FIG. 3 schematically illustrates, in similar manner to FIG. 1, another embodiment of the invention.

The scapular component of the embodiment of FIG. 1 comprises an L-shaped member 10 of generally strip form having a first, shorter arm 11 and a second, longer arm 12 mutually perpendicularly angled. The longer arm 12 is outwardly cranked at 13 partway along its length and the free end portion of this arm has its inner face formed to define a part-spherical concave surface 14. The surface 14 is of shallow minor-segmental shape and opens into the side faces of the arm so that the surface is elongated. The outer faces of the arms 11 and 12 are each formed with shallow relieved configurations 15 by the provision of ribs, grooves, studs or similar formations.

The associated humeral component comprises a solid, substantially hemispherical bearing part 20 to define a convex hemispherical surface 21 of equal radius to that of the concave surface 14. The diametral face of the part 20 has a tapered stem 22 projecting integrally perpendicularly from its centre to a distance not greater than the diameter of part 20, and this stem has circumferential grooves 23 therearound.

The intended locations of these components are shown in FIG. 1 relative to the scapula and humerus which are respectively shown, in part, at 30 and 40. As indicated in the above introductory discussion, the scapula is shaped, following removal of the rotator mechanism above the humeral head, to receive the scapular component, as shown, with its shorter arm disposed below the coracoid process and its longer arm depended therefrom with the cranked portion seated in the site of the natural glenoid cavity. The scapular component is secured in this position by use of acrylic or other bone cement keyed with exposed cancellous bone in the scapula and with the relieved configurations of the component. The humeral component is located, as shown, to replace the articular part of the humeral head following removal of the latter by an appropriate section and drilling or reaming of the exposed cancellous bone or medullary canal to receive the stem 22. Again securement is effected with bone cement.

The overall result is to provide a total arthroplasty unconstrained except by natural elements, allowing extensive articulation, and not requiring extensive bone removal or penetration. Regarding the first feature of this result: there is clearly no direct mechanical linkage between the two components except for the inter-engagement of their bearing surfaces. As to the second feature: the natural joint situation is closely simulated since the glenoid cavity and humeral head articulating surfaces are replaced by bearing surfaces which substantially duplicate the form surfaces in shape and size, while at the same time other parts of the components, namely the first arm of the scapular component are adequately spaced from the zone of articulation to avoid undesired limitations on movement. The remaining feature is self-evident from FIG. 1, while at the same time adequate securement is possible, particularly in respect of the scapular, bearing in mind the fact that any tendency for loosening of the components is reduced by a reduction of constraints within the prosthetic mechanism and transmission of forces therethrough, and also by a reduction of bearing surface engagement, to more closely simulate the natural condition.

While the invention has been described so far with more particular reference to the embodiment of FIG. 1, it is not intended to be limited thereby. Indeed some modification is contemplated in further development of the invention, and such modification is exemplified by the embodiment of FIG. 3. In this second embodiment, the scapular component is modified by thickening of the shorter arm of the L-shape to accommodate extension of the concave bearing surface. This enhances stability without significantly reducing the range of articulation relative to that of the natural joint. Also, the humeral component is shown in a hollowed cap form of which the inner surface is suitably grooved to key with the associated cement. The convex surface of this cap can be extended relative to the corresponding surface in FIG. 1, but there need be no increase in bone removal.

We claim:

1. An endoprosthetic shoulder joint device, comprising:
   a humeral component including a bearing part defining a substantially part-spherical, convex bearing surface
   and a scapular component including a generally L-shaped member having one arm of said L-shaped member longer than the other such arm, having its inner face formed to define a substantially part-spherical, concave bearing surface of which at least part lies in said one arm, and having said one arm of cranked form at least in its outer face;
   said bearing surfaces being engaged for mutual articulation between said components;
   and said part and said member being adapted remotely from said bearing surfaces for respective securement to the humerus and scapular.

2. A device according to claim 1 wherein said concave bearing surface is wholly formed in the free end porition of said one arm.

3. A device according to claim 1 wherein said other arm is thicker than said one arm as seen in the side view of said L-shape, and said concave bearing surface extends into both said arms.

4. A device according to claim 1 wherein said concave bearing surface opens into the side edge faces of said member.

5. A device according to claim 1 wherein said adaption of said member comprises a relieved configuration which is shallow relative to the thickness of such member.

6. A device according to claim 1 wherein said humeral component part comprises a substantially spherical segmental solid having a stem projecting from the chordal face of such solid, said stem being no longer than the diameter of said solid.

7. A device according to claim 1 wherein said humeral component part comprises a hollowed cap of substantially spherical segmental external shape, the hollow of said cap being grooved.

8. The use of an endoprosthetic shoulder joint device including a first component having a bearing part defining a substantially part-spherical, convex bearing surface; and a second component having a generally L-shaped member having its inner face formed to define a substantially part-spherical, concave bearing surface therein, which concave surface is complementary with said convex surface, said use comprising:
   securing said first component to the humerus to substitute said convex surface for the natural articular surface thereof at the humero - scapular joint;
   securing said second component to the scapular with one arm of said L-shaped member located on the underside of the acromion, and the other arm of said L-shaped member extending across the site of the scapular glenoid cavity, to substitute said concave surface for said cavity;
   and bringing said surfaces into articular engagement.

* * * * *